(12) United States Patent
Arai et al.

(10) Patent No.: US 11,311,262 B2
(45) Date of Patent: Apr. 26, 2022

(54) INFORMATION PROCESSING APPARATUS AND PROGRAM

(71) Applicant: FUJIFILM Corporation, Tokyo (JP)

(72) Inventors: Takahisa Arai, Kanagawa (JP);
Takeyasu Kobayashi, Kanagawa (JP);
Shunsuke Kodaira, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 179 days.

(21) Appl. No.: 16/788,314

(22) Filed: Feb. 12, 2020

(65) Prior Publication Data

US 2020/0261045 A1 Aug. 20, 2020

(30) Foreign Application Priority Data

Feb. 14, 2019 (JP) .............................. JP2019-024728

(51) Int. Cl.
*A61B 6/00* (2006.01)
*A61B 6/04* (2006.01)
(52) U.S. Cl.
CPC ............ *A61B 6/502* (2013.01); *A61B 6/0414* (2013.01); *A61B 6/0435* (2013.01); *A61B 6/5211* (2013.01)
(58) Field of Classification Search
CPC ....... A61B 6/04; A61B 6/0407; A61B 6/0414; A61B 6/0435; A61B 6/463; A61B 6/502; A61B 6/5217; A61B 6/5294; A61B 6/542; A61B 6/544; A61B 6/58; A61B 6/582; A61B 2576/02; H01J 37/02; H01J 37/023; H01J 37/20; H01J 2237/02; H01J 2237/024; H01J 2237/20; H01J 2237/2007; H01J 2237/20278; H01J 2237/20285; G01N 2223/03; G01N 2223/04; G01N 2223/30; G01N 2223/302; G01N 2223/303; G01N 2223/306; G01N 2223/321; G01N 2223/40; G01N 2223/401; G01N 2223/405; G01N 2223/408; G01N 2223/612; G01N 2223/6126
See application file for complete search history.

(56) References Cited

U.S. PATENT DOCUMENTS

| | | | | |
|---|---|---|---|---|
| 2003/0095624 A1* | 5/2003 | Eberhard | ............... | A61B 6/502 378/37 |
| 2012/0063566 A1* | 3/2012 | Smith | ................... | A61B 6/502 378/37 |
| 2017/0367675 A1* | 12/2017 | Arai | ..................... | A61B 6/0414 |

FOREIGN PATENT DOCUMENTS

JP 2010069241 4/2010

* cited by examiner

*Primary Examiner* — Anastasia Midkiff
(74) *Attorney, Agent, or Firm* — JCIPRNET (57) ABSTRACT

A console (information processing apparatus) of a mammography apparatus includes: a compression conditions acquisition unit that acquires a compression force and a compression thickness measured in the imaging of a first breast that is one of a right breast and a left breast; a compression conditions estimation unit that, in the case of imaging a second breast that is the other one of the right breast and the left breast, estimates a compression force and a compression thickness of the second breast using the compression force and the compression thickness of the first breast; and a display unit that displays the compression force and the compression thickness estimated by the compression conditions estimation unit at least in imaging of the second breast.

10 Claims, 7 Drawing Sheets

| | LEFT BREAST (IMAGED) | RECOMMENDED RANGE IN IMAGING OF LEFT BREAST |
|---|---|---|
| COMPRESSION THICKNESS | 45 mm | 40 TO 50 mm |
| COMPRESSION FORCE | 100 N | 80 TO 120 N |

INFORMATION PROCESSING APPARATUS AND PROGRAM

CROSS-REFERENCE TO RELATED APPLICATIONS

This application claims priority under 35 U.S.C. § 119(a) to Japanese Patent Application No. 2019-024728 filed on 14 Feb. 2019. The above application is hereby expressly incorporated by reference, in its entirety, into the present application.

BACKGROUND OF THE INVENTION

1. Field of the Invention

The present invention relates to an information processing apparatus and a program using a mammography image obtained by imaging the breast of a subject using radiation, such as X-rays.

2. Description of the Related Art

In the medical field, mammography apparatuses for imaging the breast of a subject using radiation, such as X-rays, have been widely used. In the case of examining a breast cancer or the like using a mammography apparatus, the breasts on both the left and right sides of the subject are usually imaged. In addition, the mammography apparatus usually performs imaging while compressing the breast flat. This is for fixing the breast, imaging the entire breast by preventing the overlap of mammary gland tissues, improving the contrast, reducing the exposure dose, and the like. In addition, there is known a breast tomography apparatus (so-called mammogram computed tomography (CT) apparatus) that automatically stops imaging in a case where there is an abnormality in the pressure at the time of compression and its distribution (JP2010-069241A).

SUMMARY OF THE INVENTION

In a case where the breast is not appropriately compressed, the overlap of mammary gland tissues may increase to cause a problem that appropriate diagnosis cannot be performed. In this case, the burden on the subject or the like, such as requiring re-imaging, increases.

In order to prevent such imaging failures, there is no choice but to perform imaging while appropriately compressing the breasts. However, since there are individual differences in breasts in terms of size, thickness, shape, elasticity, and the like, it is not easy to find appropriate compression conditions that match the characteristics of the breast and position the breast properly. In addition, even in a case where attention is paid to a specific subject, there are many cases where the above-described characteristics are different between the left and right breasts. For this reason, breast positioning under the appropriate compression conditions is not easy. The breast positioning is difficult unless the person is a skilled radiology technician or doctor (hereinafter, referred to as a radiology technician or the like). In particular, in a case where the skill level of the radiology technician or the like who operates the mammography apparatus is low, it is difficult to find appropriate compression conditions that match the characteristics of the breast, and there is a tendency for imaging failures to increase due to a breast positioning error.

It is an object of the invention to provide an information processing apparatus and a program for supporting a reduction in imaging failures due to failure of breast positioning.

An information processing apparatus of the invention comprises: a compression conditions acquisition unit that acquires a compression force and a compression thickness, which is a thickness after compression, for a first breast that is one of a right breast that is a breast on a right side of a subject and a left breast that is a breast on a left side of the subject, the compression force and the compression thickness being measured in imaging of the first breast; a compression conditions estimation unit that, in a case of imaging a second breast that is the other one of the right breast and the left breast, estimates a compression force and a compression thickness of the second breast using the compression force and the compression thickness of the first breast; and a display unit that displays the compression force and the compression thickness estimated by the compression conditions estimation unit at least in imaging of the second breast.

It is preferable that the compression conditions estimation unit estimates a range of a compression force and a range of a compression thickness.

It is preferable that the compression conditions estimation unit estimates a value of a compression force and a value of a compression thickness.

It is preferable that the compression conditions estimation unit estimates the compression force and the compression thickness of the second breast using a learned model that outputs the compression force and the compression thickness of the second breast in response to an input of the compression force and the compression thickness of the first breast.

Another information processing apparatus of the invention comprises: a compression conditions acquisition unit that acquires a compression force and a compression thickness, which is a thickness after compression, for a right breast and a compression force and a compression thickness, which is a thickness after compression, for a left breast, the compression force and the compression thickness for the right breast being measured in imaging of the right breast that is a breast on a right side of a subject and the compression force and the compression thickness for the left breast being measured in imaging of the left breast that is a breast on a left side of the subject; a determination unit that determines whether or not positioning is possible using the compression force and the compression thickness of the right breast and the compression force and the compression thickness of the left breast; and a display unit that displays at least whether or not positioning is possible that is a determination result of the determination unit.

It is preferable that the display unit displays the compression force and the compression thickness of the right breast and the compression force and the compression thickness of the left breast.

It is preferable that, in a case where the determination result of the determination unit is a determination result indicating that positioning is impossible, the display unit performs display for prompting re-imaging.

It is preferable that the determination unit determines whether or not positioning is possible using a learned model that outputs a result indicating whether or not the positioning is possible in response to an input of the compression force and the compression thickness of the right breast and the compression force and the compression thickness of the left breast.

A program of the invention is a program for driving an information processing apparatus having a compression conditions acquisition unit that acquires a compression force and a compression thickness, which is a thickness after compression, for a first breast that is one of a right breast that is a breast on a right side of a subject and a left breast that is a breast on a left side of the subject, the compression force and the compression thickness being measured in imaging of the first breast, and a display unit that displays the estimated compression force and compression thickness in a case of imaging a second breast that is the other one of the right breast and the left breast. The program causes a computer to execute: estimating the compression force and the compression thickness of the second breast using a learned model that outputs a compression force and a compression thickness of the second breast, which is the other one of the right breast and the left breast, in response to an input of the compression force and the compression thickness of the first breast.

Another program of the invention is a program for driving an information processing apparatus having a compression conditions acquisition unit that acquires a compression force and a compression thickness, which is a thickness after compression, for a right breast and a compression force and a compression thickness, which is a thickness after compression, for a left breast, the compression force and the compression thickness for the right breast being measured in imaging of the right breast that is a breast on a right side of a subject and the compression force and the compression thickness for the left breast being measured in imaging of the left breast that is a breast on a left side of the subject, and a display unit that displays whether or not positioning is possible. The program causes a computer to execute: determining whether or not positioning is possible using a learned model that outputs a result indicating whether or not the positioning is possible in response to an input of the compression force and the compression thickness of the right breast and the compression force and the compression thickness of the left breast.

According to the information processing apparatus and the program of the invention, it is possible to reduce imaging failures due to failure of breast positioning.

DESCRIPTION OF THE PREFERRED EMBODIMENTS

First Embodiment

Figure 1:
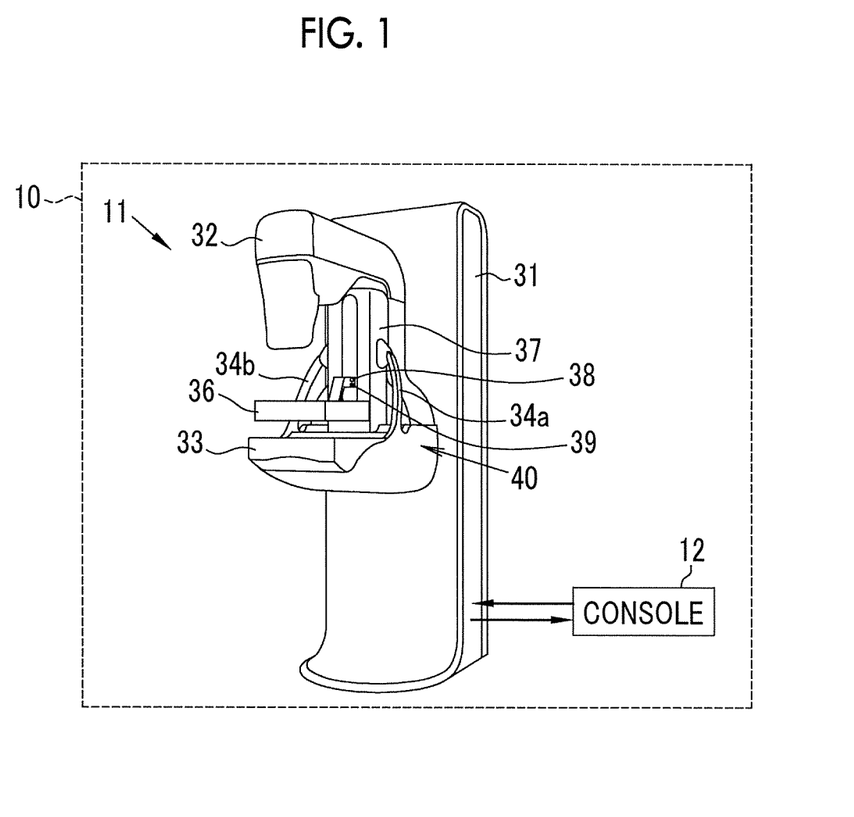
FIG. 1 is an explanatory diagram showing the configuration of a mammography apparatus.

As shown in FIG. 1, a mammography apparatus 10 that is an example of a radiographic imaging apparatus comprises an apparatus body 11 that images the breast of a subject using X-rays that are radiation and a console 12 that controls the apparatus body 11.

The apparatus body 11 comprises a support 31, an X-ray generation unit 32, an imaging table 33 in which an X-ray imaging unit is provided, a compression plate 36, an elevating unit 37, and the like. The X-ray generation unit 32 and the imaging table 33 are integrated to form a movable unit 40 that performs position adjustment according to the subject in the apparatus body 11.

The X-ray generation unit 32 includes at least an X-ray tube that generates X-rays. Therefore, in the mammography apparatus 10, the X-ray generation unit 32 is a radiation generation unit that generates radiation (X-rays). In addition, the X-ray generation unit 32 can include a high voltage circuit that supplies a high voltage for generating X-rays to the X-ray tube. That is, the X-ray generation unit 32 can be configured by a so-called mono tank.

The imaging table 33 is a stage on which the breast is placed, and the breast is interposed between the imaging table 33 and the compression plate 36 at the time of imaging. In addition, the imaging table 33 configures a radiographic imaging unit that images the breast of the subject using radiation (X-rays). The imaging table 33 includes, as the radiographic imaging unit, for example, a flat panel detector (FPD) for imaging the breast using radiation and a grid for removing scattered radiation (static type Lysholm brande or mobile type Bucky brande). The mammography apparatus 10 has a plurality of types of grids that can be exchanged according to imaging conditions, and can also perform imaging without using a grid. In addition, a gripping unit 34a that the subject grips with the right hand and a gripping unit 34b that the subject grips with the left hand are attached to the imaging table 33. The gripping unit 34a and the gripping unit 34b are so-called armrests. Since X-rays are used in the present embodiment, the radiographic imaging unit is specifically an X-ray imaging unit.

In imaging, the compression plate 36 compresses the breast of the subject placed on the imaging table 33 to make the breast flat. This is to reduce the overlap of normal mammary glands so that it becomes easy to find lesion candidates, such as calcifications. In addition, a compression force sensor 38 that detects and outputs a force with which the breast of the subject is compressed by the compression plate 36 (hereinafter, referred to as a compression force) is attached to the compression plate 36. For this reason, in a case where imaging is performed to obtain a mammography image, the mammography apparatus 10 can obtain the compression force in the imaging using the compression force sensor 38. In addition, a compression thickness sensor 39 that detects and outputs the distance between the compression plate 36 and the imaging table 33, that is, the thickness of the compressed breast (hereinafter, referred to as a compression thickness) is attached to the compression plate 36. For this reason, in a case where imaging is performed to obtain a mammography image, it is possible to obtain the compression thickness in the imaging using the compression thickness sensor 39.

The elevating unit 37 moves the compression plate 36 up and down with respect to the imaging table 33. In this manner, the elevating unit 37 supports the compression plate 36 almost in parallel to the imaging table 33 and at a specific distance according to the thickness of the breast.

The movable unit 40 can freely rotate within a predetermined angle range while maintaining the relative position and direction of the X-ray generation unit 32 and the imaging table 33. Therefore, the apparatus body 11 can perform imaging in a state in which the imaging table 33 is horizontally disposed or the imaging table 33 is disposed so as to be inclined from the horizontal plane. Specifically, the apparatus body 11 can perform craniocaudal imaging (CC imaging) for imaging the breast from the head-to-tail direction by arranging the imaging table 33 in the horizontal direction. The apparatus body 11 can perform mediolateral oblique imaging (MLO imaging) for imaging the breast from the internal and external oblique directions by arranging the imaging table 33 so as to be inclined.

The X-ray generation unit 32 of the movable unit 40 can move rotationally within a predetermined range while fixing the positions of the imaging table 33 and the compression plate 36. Therefore, the apparatus body 11 can perform so-called stereo imaging and tomosynthesis imaging. The stereo imaging is an imaging mode in which the breast of the subject fixed at a specific position and direction (for example, position and direction of CC imaging) is imaged from one inclined direction or a plurality of inclined directions having different inclination angles to obtain a perspective image (hereinafter, referred to as a stereo image) from the inclined direction. The tomosynthesis imaging is an imaging mode in which, for the breast of the subject fixed at a specific position and direction, a tomographic image (hereinafter, referred to as a tomosynthesis image) is obtained using images captured from a plurality of inclined directions. The compression force and the compression thickness can be acquired regardless of the imaging mode, and can be acquired for each imaging.

Figure 2:
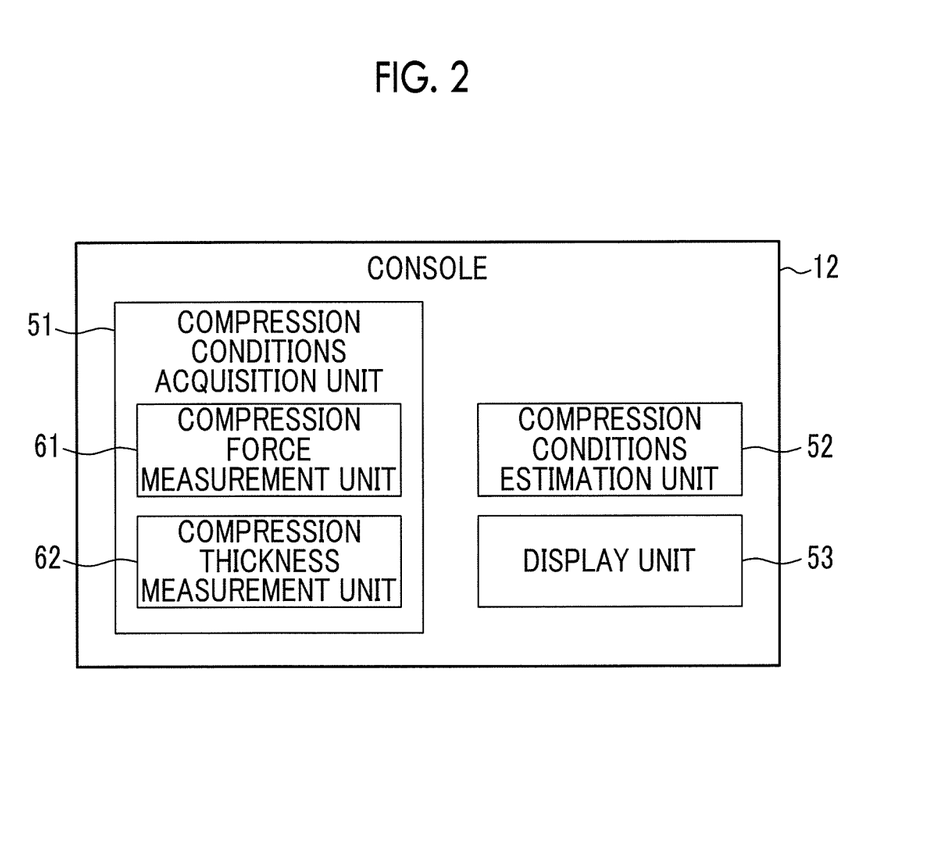
FIG. 2 is a block diagram showing the configuration of a console.

The console 12 is a control device that controls the mammography apparatus 10, and is an information processing apparatus that performs information processing using various mammography images. As shown in FIG. 2, the console 12 comprises a compression conditions acquisition unit 51, a compression conditions estimation unit 52, and a display unit 53.

The compression conditions acquisition unit 51 acquires a compression force on the breast and a compression thickness, which is the thickness of the breast after compression, in mammography imaging. For this reason, the compression conditions acquisition unit 51 comprises a compression force measurement unit 61 and a compression thickness measurement unit 62. The compression force measurement unit 61 can measure the compression force in imaging in real time using a signal output from the compression force sensor 38 at least in a case where the imaging is performed. The compression force measurement unit 61 can measure the compression force after imaging using the recording of the output of the compression force sensor 38 stored in association with the mammography image. The compression thickness measurement unit 62 can measure the compression thickness in imaging in real time at least in a case where the imaging is performed. The compression thickness measurement unit 62 can measure the compression pressure after imaging using the recording of the output of the compression thickness sensor 39 stored in association with the mammography image. In the present embodiment, the compression force measurement unit 61 continuously measures the compression force while the compression plate 36 is attached to the movable unit 40. Similarly, in the present embodiment, the compression thickness measurement unit 62 continuously measures the compression thickness while the compression plate 36 is attached to the movable unit 40. As a result, the compression conditions acquisition unit 51 acquires the imaging conditions of the compression force and the compression thickness in real time.

In the present embodiment, the compression conditions acquisition unit 51 acquires the compression force and the compression thickness in the imaging of the first breast that is one of the right breast that is the breast on the right side of the subject (hereinafter, simply referred to as a right breast) and the left breast that is the breast on the left side of the subject (hereinafter, simply referred to as a left breast). That is, the compression conditions acquisition unit 51 acquires the compression conditions (compression force and compression thickness) of the previously imaged breast (first breast) in a case where the right breast and the left breast are imaged in the same imaging mode.

In a case where the second breast that is the other one of the right breast and the left breast is imaged in the same imaging mode as for the first breast, the compression conditions estimation unit 52 estimates a suitable compression force and compression thickness in the imaging of the second breast using the compression force and the compression thickness of the first breast. For example, in the case of performing MLO imaging of the left breast after performing MLO imaging of the right breast, the compression conditions estimation unit 52 calculates a compression force and a compression thickness estimated to be suitable in the case of performing MLO imaging of the left breast using the compression force and the compression thickness in the MLO imaging of the right breast. The first breast may be either the right breast or the left breast, and the second breast may be either the left breast or the right breast depending on whether the first breast is the right breast or the left breast.

Figure 3:
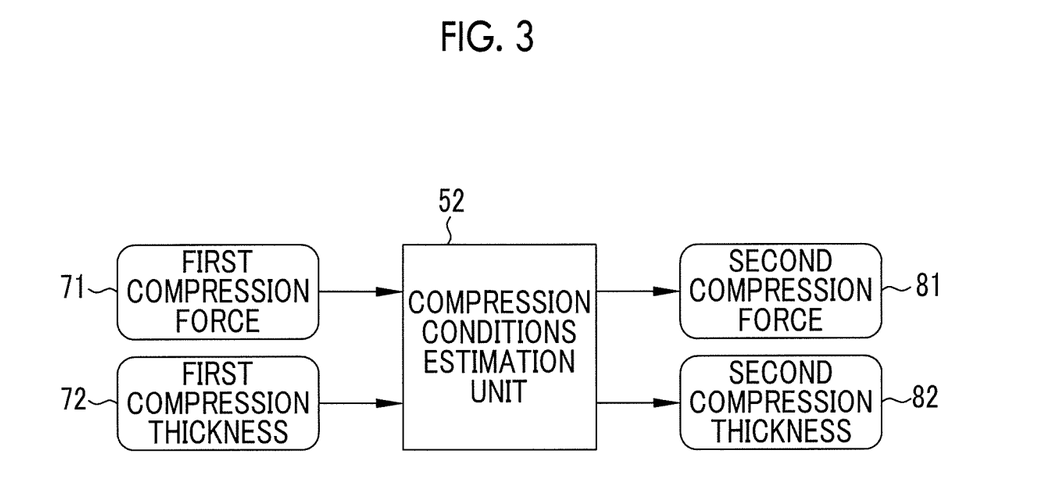
FIG. 3 is an explanatory diagram of a compression conditions estimation unit.

For example, as shown in FIG. 3, the compression conditions estimation unit 52 can be configured using a learned model (so-called artificial intelligence (AI) program) that receives an input of a first compression force 71 that is the compression force of the first breast and a first compression thickness 72 that is the compression thickness of the first breast and outputs a second compression force 81 that is a compression force recommended (or allowed) in the case of imaging the second breast in the same imaging mode as for the first breast and a second compression thickness 82 that is a compression thickness recommended (or allowed) in the case of imaging the second breast in the same imaging mode as for the first breast. In the present embodiment, the first compression force 71 and the first compression thickness 72 are specific numerical values, while the second compression force 81 output from the compression conditions estimation unit 52 is a numerical value (for example, an upper limit value and a lower limit value) indicating the range of the compression force and the second compression thickness 82 output from the compression conditions estimation unit 52 is a numerical value (for example, an upper limit value and a lower limit value) indicating the range of the compression thickness.

The display unit 53 displays the compression force and the compression thickness estimated by the compression conditions estimation unit 52 at least in the imaging of the second breast. That is, in the case of imaging the second breast in the same imaging mode as for the first breast, the display unit 53 displays the second compression force 81 and the second compression thickness 82. In this manner, the mammography apparatus 10 supports the positioning of the second breast. "Display the compression force and the compression thickness estimated at least in the imaging of the second breast" refers to presenting the compression force and the compression thickness at a timing at which the second breast can be positioned with reference to the estimated compression force and compression thickness (timing before or after imaging of the second breast (particularly preferably a timing at which the second breast is positioned)). Positioning of the breast refers to performing adjustment to keep the compression force and the compression thickness of the breast within the appropriate range (range where mammography images that can be used for diagnosis are obtained) while keeping a diagnosis target part (usually the entire breast) of the breast within the appropriate range.

In addition, the display unit 53 can display the compression force measured by the compression force measurement unit 61 and/or the compression thickness measured by the compression thickness measurement unit 62. By displaying the compression force and the compression thickness in real time together with the second compression force 81 and the second compression thickness 82 that are recommended values (recommended range), the radiology technician or the like can easily set the compression force and the compression thickness to recommended values (recommended range). Therefore, the effect of supporting the positioning in the imaging of the second breast is high.

Figure 4:
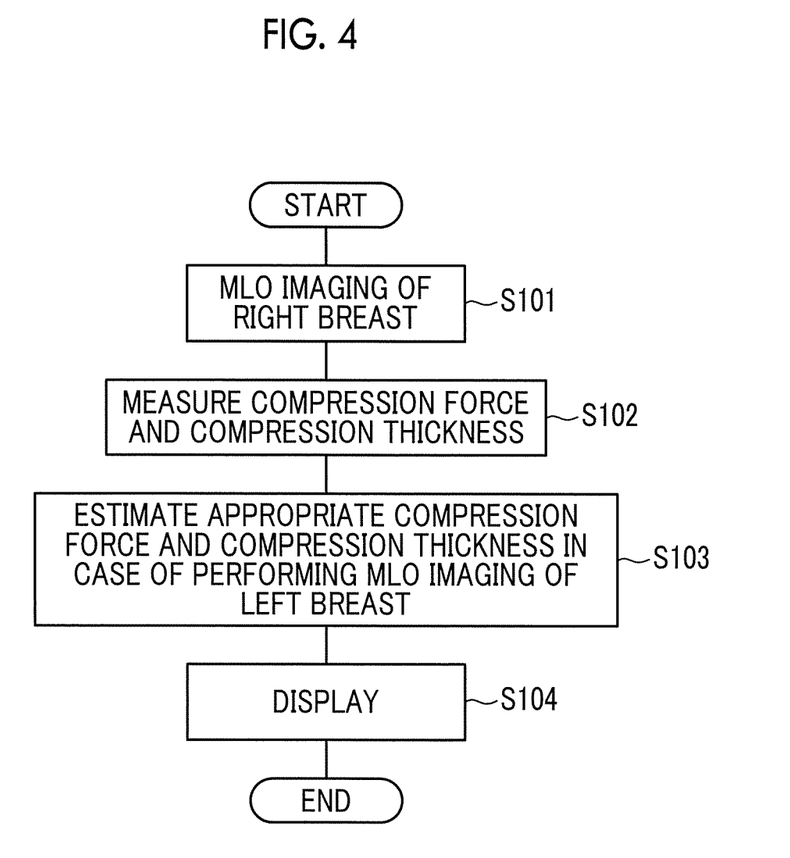
FIG. 4 is a flowchart showing the operation of the mammography apparatus.

Hereinafter, the operation of the mammography apparatus 10 configured as described above will be described. As shown in FIG. 4, for example, the right breast of the subject is MLO imaged (step S101), and then the compression force measurement unit 61 measures the compression force in the imaging, and the compression thickness measurement unit 62 measures the compression thickness in the imaging (step S102). Therefore, the compression conditions acquisition unit 51 acquires the compression force and the compression thickness (the first compression force 71 and the first compression thickness 72) in the MLO imaging of the right breast that is the first breast.

Figure 5:
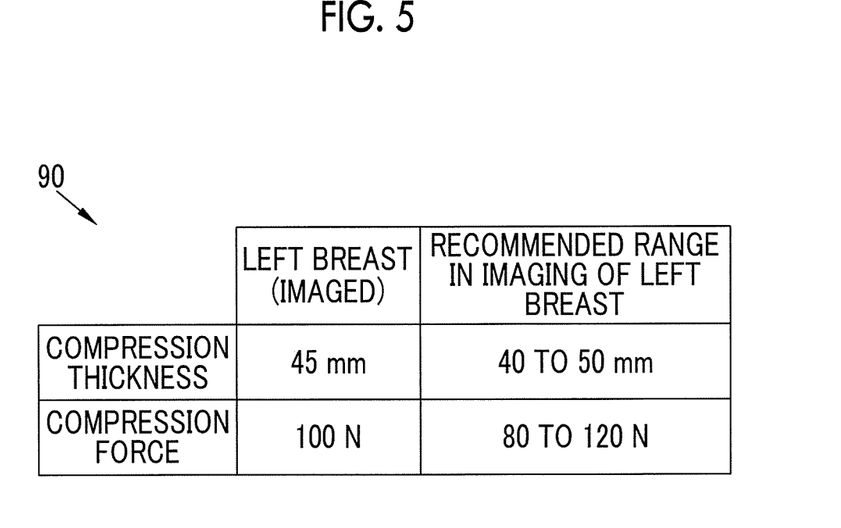
FIG. 5 is an example of the display in a display unit.

In the case of performing MLO imaging of the left breast of the same subject after ending the MLO imaging of the right breast, the compression conditions estimation unit 52 automatically estimates a compression force and a compression thickness (the second compression force 81 and the second compression thickness 82), which are recommended in the MLO imaging of the left breast, using the first compression force 71 and the first compression thickness 72 (step S103), and the display unit 53 displays the estimated compression force and compression thickness (step S104). For example, as shown in FIG. 5, the display unit 53 displays the actual compression force and compression thickness at the time of imaging of the right breast and the recommended range of the compression force and the compression thickness in the imaging of the left breast in the form of a table 90. In FIG. 5, the actual compression thickness at the time of imaging of the right breast is "45 mm", and the actual compression force at the time of imaging of the right breast is "100 Ns (Newton)". In addition, in FIG. 5, the recommended range of the compression thickness in the imaging of the left breast is "40 to 50 mm" (40 mm or more and 50 mm or less), and the recommended range of the compression force in the imaging of the left breast is "80 to 120 N" (80 Ns or more and 120 Ns or less).

As described above, in the case of imaging (in the present embodiment, MLO imaging) the left breast in the same imaging mode as for the right breast after imaging the right breast, the mammography apparatus 10 estimates and displays a compression force and a compression thickness recommended in the imaging of the left breast. Since this display is a clear guide in the positioning of the left breast, a radiology technician or the like who uses the mammography apparatus 10 positions the left breast so that the compression force and the compression thickness are within the above-described display. Therefore, it is possible to image the left breast without failure. That is, according to the mammography apparatus 10, the failure of positioning can be prevented, and as a result, imaging failures due to the failure of positioning can be reduced.

In the present embodiment, MLO imaging of the right breast and the left breast is performed. However, the mammography apparatus 10 can perform the same estimation and display even in the case of imaging the right breast and the left breast of the same subject in other imaging modes, such as CC imaging. In addition, in the present embodiment, imaging is performed from the right breast. However, the mammography apparatus 10 can perform the same estimation and display even in the case of imaging the left breast first.

In the first embodiment described above, the compression conditions estimation unit 52 estimates the compression force and the compression thickness recommended in the imaging of the second breast in the respective ranges. However, the compression conditions estimation unit 52 can estimate the compression force and the compression thickness of the second breast as pinpoint values (one numerical value for each of the compression force and the compression thickness). In a case where the compression force and the compression thickness recommended in the imaging of the second breast are estimated within the range, there is an advantage that the breast can be easily positioned in that the radiology technician or the like can easily grasp the allowable compression force and compression thickness. On the other hand, in a case where the compression force and the compression thickness recommended in the imaging of the second breast are estimated as pinpoint values, there is an advantage that the breast can be easily positioned in that the radiology technician or the like can easily and clearly grasp the compression force and the compression thickness to be targeted in the imaging of the second breast.

In the first embodiment described above, the compression conditions estimation unit 52 is the AI program itself. However, the compression conditions estimation unit 52 is not the AI program itself, but can be configured to include the AI program. For example, the compression conditions estimation unit 52 can estimate the compression force and the compression thickness in the imaging of the second breast using a learned model that outputs the compression force and the compression thickness in the imaging of the second breast in response to the input of the compression force and the compression thickness in the imaging of the first breast. For this reason, in the mammography apparatus 10, for example, the compression conditions estimation unit 52 can communicate with an information processing apparatus, an analysis apparatus, or the like in which the learned model operating in an apparatus other than the console 12 is used and estimate the compression force and the compression thickness of the second breast using the learned model. Since there is no change in the fact that the AI program is included, the case where the compression conditions estimation unit 52 is the AI program is an aspect of the case where the compression conditions estimation unit 52 includes the AI program. The determination accuracy is particularly high in a case where the compression conditions estimation unit 52 is the AI program and a case where the compression conditions estimation unit 52 includes the AI program.

Figure 6:
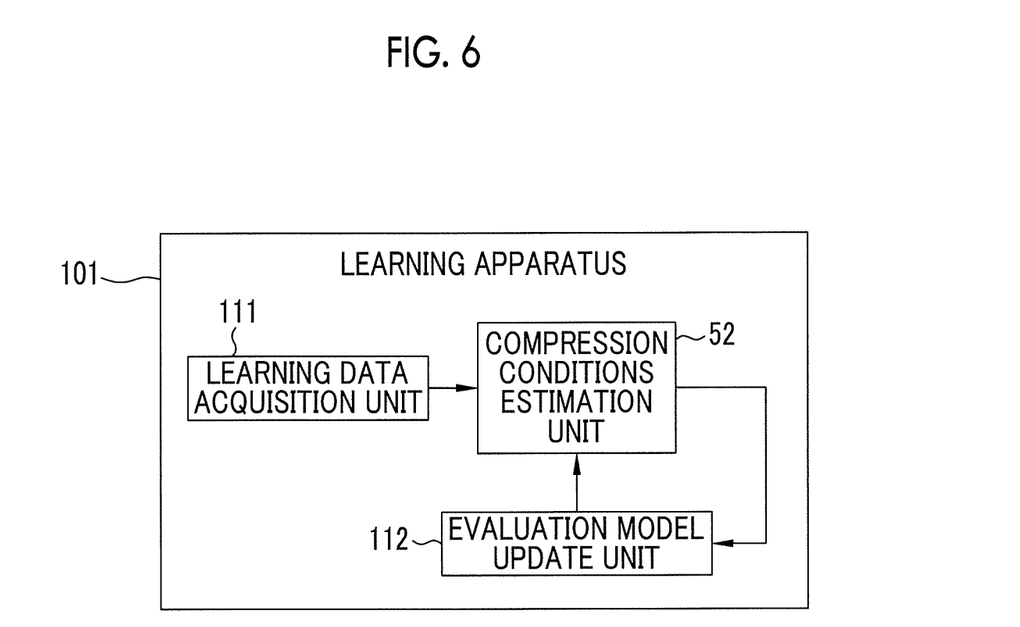
FIG. 6 is a block diagram of a learning apparatus that performs learning of the compression conditions estimation unit.

The learning of the compression conditions estimation unit 52, which is an AI program, can be performed using a learning apparatus 101 shown in FIG. 6. The learning apparatus 101 is an apparatus for learning (optimizing) the compression conditions estimation unit 52, and comprises a learning data acquisition unit 111 and an evaluation model update unit 112.

The learning data acquisition unit 111 acquires data to be used for the learning of the compression conditions estimation unit 52. Specifically, the learning data acquisition unit 111 acquires the compression force and the compression thickness at the time of imaging the right breast and the left breast of the same subject in the same imaging mode, which are the compression force and the compression thickness at the time of capturing mammography images that could be used for diagnosis. Then, the compression force and the compression thickness at the time of imaging one breast are input to the compression conditions estimation unit 52 that performs learning as explanatory variables, and the compression force and the compression thickness at the time of imaging the other breast are input to the compression conditions estimation unit 52 as correct answer labels.

The compression conditions estimation unit 52 outputs an estimated value (so-called evaluation value) of a target variable and an error between the estimated value of the target variable and the correct answer label using the compression force and the compression thickness, which are explanatory variables, and an evaluation model for acquiring a target variable from explanatory variables (for example, an evaluation function used in a specific regression analysis model). In this learning, the target variable is the range of the compression force and the compression thickness.

The evaluation model update unit 112 optimizes the value of a parameter, which is used by the compression conditions estimation unit 52 in the evaluation model, using the error between the correct answer label and the estimated value of the target variable output from the compression conditions estimation unit 52 under learning. Optimization refers to calculating a parameter that minimizes the error for a set of a plurality of explanatory variables and correct answer labels and updates a parameter used in the evaluation model to the parameter. The compression conditions estimation unit 52 becomes an optimized evaluation model (learned model) by repeating the above-described learning by the learning apparatus 101.

The learning apparatus 101 is an apparatus that performs so-called supervised learning. However, the learning of the compression conditions estimation unit 52 can be performed by unsupervised learning or reinforcement learning. In addition, the evaluation model and the optimization method may be changed according to a specific learning mode. In addition, the compression conditions estimation unit 52 may be optimized by supervised learning using an explanatory variable, a target variable, and/or an evaluation model different from the learning apparatus 101.

Second Embodiment

In the above-described first embodiment and modification examples thereof, imaging failures are reduced by displaying the recommended compression force and compression thickness. Instead of this, imaging failures can also be reduced by displaying whether or not positioning is possible.

Figure 7:
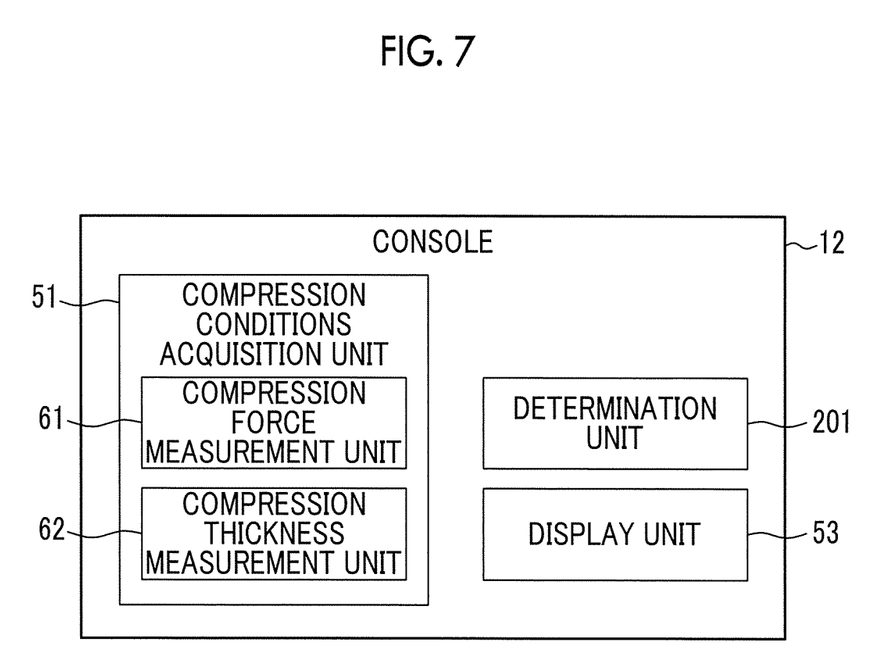
FIG. 7 is a block diagram showing the configuration of a console of a second embodiment.

In this case, for example, as shown in FIG. 7, a determination unit 201 is provided in the console 12 instead of the compression conditions estimation unit 52. The determination unit 201 determines whether or not positioning is possible using the compression force and the compression thickness measured for the imaging of the right breast and the compression force and the compression thickness measured for the imaging of the left breast. Then, the display unit 53 displays at least whether or not positioning is possible that is the determination result of the determination unit 201.

Figure 8:
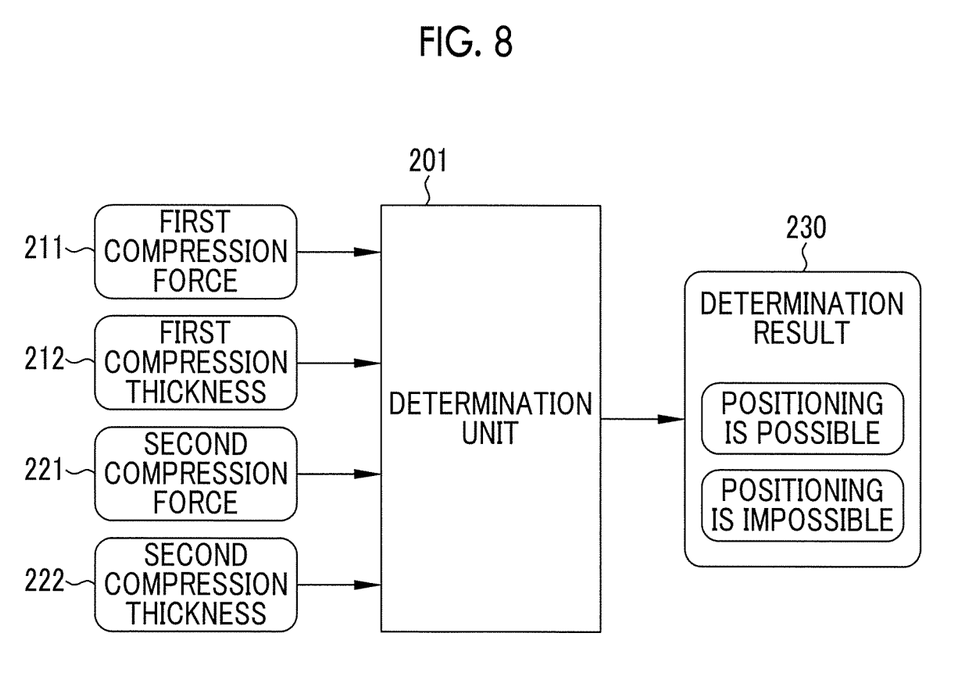
FIG. 8 is an explanatory diagram of a determination unit.

For example, as shown in FIG. 8, the determination unit 201 can be configured by a learned model that receives an input of a first compression force 211 that is the compression force of the right breast, a first compression thickness 212 that is the compression thickness of the right breast, a second compression force 221 that is the compression force of the left breast and a second compression thickness 222 that is the compression thickness of the left breast and outputs a determination result 230 of "positioning is possible" or "positioning is impossible" in the imaging of the breast (right breast and left breast) of the subject. In this case, the determination unit 201 is a classifier that classifies the combinations of the first compression force 211, the first compression thickness 212, the second compression force 221, and the second compression thickness 222 as positioning possible or positioning impossible.

In a case where the determination unit 201 is provided in the console 12 as described above, as shown in FIG. 9, for example, the right breast of the subject is MLO imaged (step S201), and then the compression force measurement unit 61 measures the compression force in the imaging, and the compression thickness measurement unit 62 measures the compression thickness in the imaging (step S202). Therefore, the compression conditions acquisition unit 51 acquires the compression force and the compression thickness (the first compression force 211 and the first compression thickness 212) in the imaging of the right breast. Thereafter, the left breast of the subject is MLO imaged (step S203), and then the compression force measurement unit 61 measures the compression force in the imaging, and the compression thickness measurement unit 62 measures the compression thickness in the imaging (step S204). Therefore, the compression conditions acquisition unit 51 acquires the compression force and the compression thickness (the second compression force 221 and the second compression thickness 222) in the imaging of the left breast in addition to the previously acquired compression force and compression thickness in the imaging of the right breast.

Figure 9:
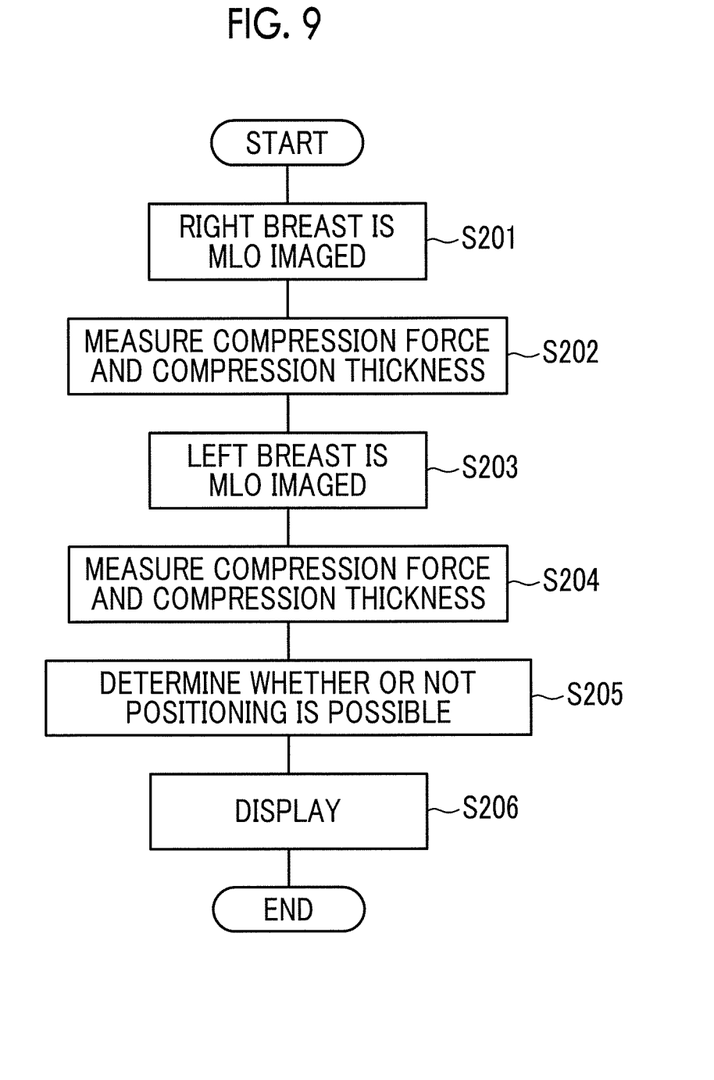
FIG. 9 is a flowchart showing the operation of a mammography apparatus of the second embodiment.
Figure 10:
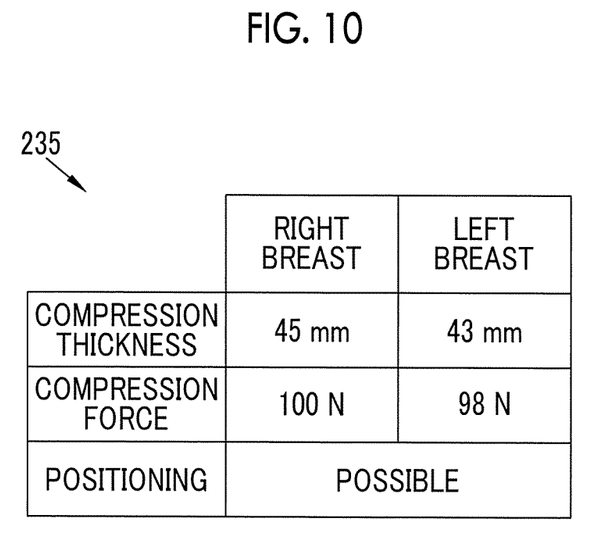
FIG. 10 is an example of the display in a display unit.

In a case where the compression conditions acquisition unit 51 acquires the compression force and the compression thickness for the left and right breasts as described above, the determination unit 201 determines whether or not positioning is possible using the acquired compression force and compression thickness (step S205), and the display unit 53 displays the determination result of "positioning is possible" or "positioning is impossible" (step S206). For example, as shown in FIG. 10, the display unit 53 displays the actual compression force and compression thickness at the time of imaging of the right breast, the actual compression force and compression thickness at the time of imaging of the left breast, and the determination result regarding whether or not positioning is possible in the form of a table 235. In FIG. 10, the actual compression thickness at the time of imaging of the right breast is "45 mm", the actual compression force at the time of imaging of the right breast is "100 N", the actual compression thickness at the time of imaging of the left breast is "43 mm", the actual compression force at the time of imaging of the left breast is "98 N". In FIG. 10, the determination result of the determination unit 201 is positioning possible.

As described above, since the mammography apparatus 10 determines whether or not positioning is possible and displays the result, it is possible to prevent the imaging from being ended while the imaging has failed. As a result, imaging failures can be reduced. For example, in a case where the determination result indicates that positioning is impossible, the radiology technician or the like can immediately perform the imaging of the left breast and/or the right breast again on the spot by looking at the display of the determination result. As a result, only the mammography image whose determination result is substantially "positioning is possible" is provided for diagnosis. For this reason, in a stage in which a mammography image is used for diagnosis, it is possible to reduce imaging failures due to breast positioning.

As shown in the second embodiment described above, it is preferable that the display unit 53 displays the compression force and compression thickness of the right breast and the compression force and compression thickness of the left breast. This is because, in a case where the determination result is "positioning is impossible", it is easy to grasp the cause. Specifically, the display of the compression force and the compression thickness at the time of imaging of the left and right breasts serves as a material to determine whether the radiology technician or the like should image the right breast again, or should image the left breast again, or should image both the left and right breasts again. Therefore, by displaying these, re-imaging can be performed smoothly while suppressing the exposure dose even in a case where positioning is impossible.

In the second embodiment described above, in a case where the determination result of the determination unit 201 is a determination result indicating that positioning is impossible, it is preferable that the display unit 53 performs display for prompting re-imaging (for example, display of a message or a warning color). This is for promoting re-imaging more directly to reliably prevent imaging failures in a case where positioning is impossible.

In the second embodiment described above, the determination unit 201 is the AI program itself. However, the determination unit 201 is not the AI program itself, but can be configured to include the AI program. For example, the determination unit 201 can determine whether or not positioning is possible using a learned model that outputs a result indicating whether or not positioning is possible in response to the input of the compression force and compression thickness of the right breast and the compression force and compression thickness of the left breast. For this reason, in the mammography apparatus 10, for example, the determination unit 201 can communicate with the above-described learned model that operates in an apparatus other than the console 12 and determine whether or not positioning is possible using the learned model. Since there is no change in the fact that the AI program is included, the case where the determination unit 201 is the AI program is an aspect of the case where the determination unit 201 includes the AI program. The determination accuracy is particularly high in a case where the determination unit 201 is the AI program and a case where the determination unit 201 includes the AI program.

Figure 11:
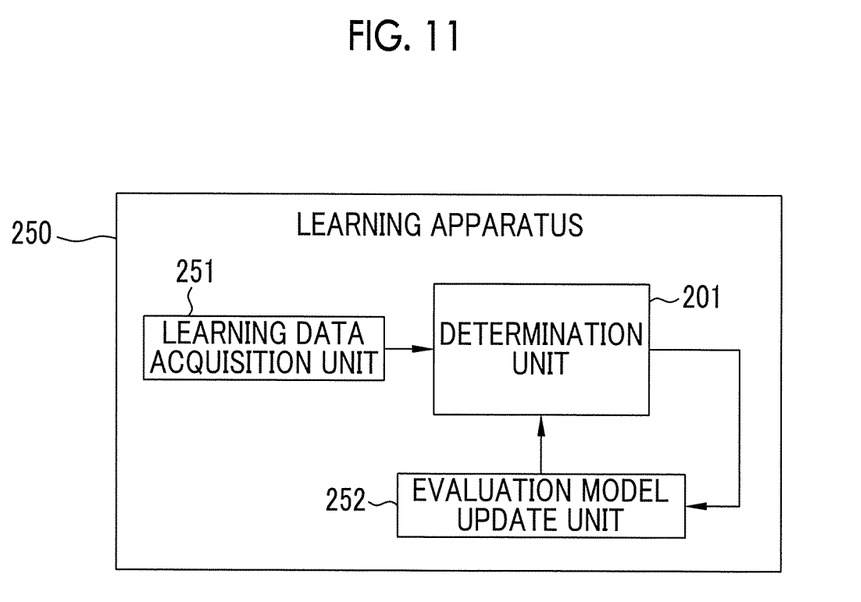
FIG. 11 is a block diagram of a learning apparatus that performs learning of a determination unit.

The learning of the determination unit 201, which is an AI program, can be performed using a learning apparatus 250 shown in FIG. 11. The learning apparatus 250 is an apparatus for learning (optimizing) the determination unit 201, and comprises a learning data acquisition unit 251 and an evaluation model update unit 252.

The learning data acquisition unit 251 acquires data to be used for the learning of the determination unit 201. Specifically, the learning data acquisition unit 251 acquires the compression force and the compression thickness at the time of imaging the right breast and the left breast of the same subject in the same imaging mode and information indicating whether or not positioning is possible (information indicating whether or not a mammography image can be used for diagnosis). Then, the compression force and the compression thickness at the time of imaging the left and right breasts are input to the determination unit 201 as explanatory variables, and the information indicating whether or not positioning is possible is input to the determination unit 201 to learn as correct answer labels.

The determination unit 201 outputs an evaluation value for estimating a target variable and an error of the evaluation value (allowable error range) using the compression force and the compression thickness, which are explanatory variables, and an evaluation model for acquiring a target variable from explanatory variables (for example, an evaluation function used in a specific regression analysis model). In this learning, the target variable is the classification of positioning possible or positioning impossible.

The evaluation model update unit 252 optimizes the value of a parameter, which is used by the determination unit 201 in the evaluation model, using the correct answer label and the evaluation value and the error output from the determination unit 201 under learning. For this reason, the determination unit 201 becomes an optimized evaluation model (learned model) by repeating the above-described learning by the learning apparatus 250.

The learning apparatus 250 is an apparatus that performs so-called supervised learning. However, the learning of the determination unit 201 can be performed by unsupervised learning or reinforcement learning. In addition, the evaluation model and the optimization method may be changed according to a specific learning mode. In addition, the determination unit 201 may be optimized by supervised learning using an explanatory variable, a target variable, and/or an evaluation model different from the learning apparatus 250.

In the above-described embodiments, modification examples thereof, and the like, the compression force is used. However, instead of the compression force or together with the compression force, data of the pressure (compression pressure) with which the breast is compressed by the compression plate 36 can be used, estimated, and/or displayed.

In addition, the compression conditions estimation unit 52 can receive the input of information relevant to the breast, such as the size, shape, and/or hardness (elasticity) of the breast, instead of the compression force and/or the compression thickness or together with the compression force and/or the compression thickness and output the compression conditions to be recommended. Similarly, the determination unit 201 can receive the input of information relevant to the breast, such as the size, shape, and/or hardness (elasticity) of the breast, instead of the compression force and/or the compression thickness or together with the compression force and/or the compression thickness and determine whether or not positioning is possible. In this manner, the accuracy of estimation and determination is improved by taking information relevant to the breast into consideration.

The compression conditions estimation unit 52 can receive the input of biological information instead of the compression force and/or the compression thickness of the breast or in addition to the compression force and/or the compression thickness of the breast and output the compression conditions to be recommended. The biological information is, for example, the subject's height, weight, age, and the presence or absence of a disease or treatment that causes changes in the characteristics of the breast. In addition, the biological information can include information of the race or the region (country, prefecture, state, province, and the like) where the subject resides. Since the characteristics of the breast may differ depending on the race or the like, the estimation accuracy is improved by taking the biological information into consideration as described above. Similarly, the determination unit 201 can receive the input of the above-described biological information instead of the compression force and/or the compression thickness of the breast or in addition to the compression force and/or the compression thickness of the breast and determine whether or not positioning is possible. By taking the biological information into consideration as described above, the determination accuracy of the determination unit 201 is improved.

In the above-described embodiments, modification examples thereof, and the like, the console 12 functions as an information processing apparatus. However, another information processing apparatus (such as a computer that functions as an analysis apparatus) that cooperates with the console 12 may have a function as an information processing apparatus of the console 12. In addition, the apparatus body 11 may have a function as an information processing apparatus of the console 12 in the above-described embodiments, modification examples thereof, and the like. In a case where the console 12 or the apparatus body 11 has a function as an information processing apparatus of the console 12 in the above-described embodiments, modification examples thereof, and the like, the entire mammography apparatus 10 functions as the information processing apparatus. In addition, the function as the information processing apparatus of the console 12 in the above-described embodiments, modification examples thereof, and the like can be distributed and implemented in a plurality of apparatuses (such as a plurality of computers).

In the embodiments described above, the hardware structures of processing units for executing various kinds of processing, such as the compression conditions acquisition unit 51, the compression force measurement unit 61, the compression thickness measurement unit 62, the compression conditions estimation unit 52, the learning data acquisition unit 111, the evaluation model update unit 112, the determination unit 201, the learning data acquisition unit 251, and the evaluation model update unit 252, are various processors shown below. The various processors include a central processing unit (CPU) that is a general-purpose processor that executes software (program) to function as various processing units, a programmable logic device (PLD) that is a processor whose circuit configuration can be changed after manufacture, such as a graphical processing unit (GPU) and a field programmable gate array (FPGA), and a dedicated electric circuit that is a processor having a circuit configuration that is designed for exclusive use in order to execute various kinds of processing.

One processing unit may be configured by one of various processors, or may be a combination of two or more processors of the same type or different types (for example, a combination of a plurality of FPGAs, a combination of a CPU and an FPGA, or a combination of a CPU and a GPU). Alternatively, a plurality of processing units may be configured by one processor. As an example of configuring a plurality of processing units using one processor, first, as represented by a computer, such as a client or a server, there is a form in which one processor is configured by a combination of one or more CPUs and software and this processor functions as a plurality of processing units. Second, as represented by a system on chip (SoC) or the like, there is a form of using a processor that realizes the function of the entire system including a plurality of processing units with one integrated circuit (IC) chip. Thus, various processing units are configured by using one or more of the above-described various processors as a hardware structure.

More specifically, the hardware structure of these various processors is an electrical circuit (circuitry) in the form of a combination of circuit elements, such as semiconductor elements.

EXPLANATION OF REFERENCES

10: mammography apparatus
11: apparatus body
12: console
31: support
32: X-ray generation unit
33: imaging table
34*a*: gripping unit
34*b*: gripping unit
36: compression plate
37: elevating unit
38: compression force sensor
39: compression thickness sensor
40: movable unit
51: compression conditions acquisition unit
52: compression conditions estimation unit
53: display unit
61: compression force measurement unit
62: compression thickness measurement unit
71: first compression force
72: first compression thickness
81: second compression force
82: second compression thickness
90: table
101: learning apparatus
111: learning data acquisition unit
112: evaluation model update unit
201: determination unit
211: first compression force
212: first compression thickness
221: second compression force
222: second compression thickness
230: determination result
235: table
250: learning apparatus
251: learning data acquisition unit
252: evaluation model update unit
S101 to S206: operation step

What is claimed is:
1. An information processing apparatus, comprising:
a processor configured to:
acquire a compression force and a compression thickness, which is a thickness after compression, for a first breast that is one of a right breast that is a breast on a right side of a subject and a left breast that is a breast on a left side of the subject, the compression force and the compression thickness being measured in imaging of the first breast; and in a case of imaging a second breast that is the other one of the right breast and the left breast, estimate a compression force and a compression thickness of the second breast using the compression force and the compression thickness of the first breast; and a display that displays the compression force and the compression thickness estimated by the processor at least in imaging of the second breast.

2. The information processing apparatus according to claim 1, wherein the processor estimates a range of a compression force and a range of a compression thickness.

3. The information processing apparatus according to claim 1, wherein the processor estimates a value of a compression force and a value of a compression thickness.

4. The information processing apparatus according to claim 1, wherein the processor estimates the compression force and the compression thickness of the second breast using a learned model that outputs the compression force and the compression thickness of the second breast in response to an input of the compression force and the compression thickness of the first breast.

5. An information processing apparatus, comprising:

a processor configured to:

acquire a compression force and a compression thickness, which is a thickness after compression, for a right breast and a compression force and a compression thickness, which is a thickness after compression, for a left breast, the compression force and the compression thickness for the right breast being measured in imaging of the right breast that is a breast on a right side of a subject and the compression force and the compression thickness for the left breast being measured in imaging of the left breast that is a breast on a left side of the subject; and determine whether or not positioning the left breast and the right breast during an instance of imaging is possible using the compression force and the compression thickness of the right breast and the compression force and the compression thickness of the left breast so as to generate a determination result; and a display that displays at least whether or not positioning the left breast and the right breast during the instance of imaging is possible that is a according to the determination result of the processor.

6. The information processing apparatus according to claim 5, wherein the display displays the compression force and the compression thickness of the right breast and the compression force and the compression thickness of the left breast.

7. The information processing apparatus according to claim 5, wherein, in a case where the determination result of the processor is a determination result indicating that positioning is impossible, the display performs display for prompting re-imaging.

8. The information processing apparatus according to claim 5, wherein the processor determines whether or not positioning is possible using a learned model that outputs a result indicating whether or not the positioning is possible in response to an input of the compression force and the compression thickness of the right breast and the compression force and the compression thickness of the left breast.

9. A non-transitory device-readable medium for storing a device-executable program for driving an information processing apparatus having a processor that acquires a compression force and a compression thickness, which is a thickness after compression, for a first breast that is one of a right breast that is a breast on a right side of a subject and a left breast that is a breast on a left side of the subject, the compression force and the compression thickness being measured in imaging of the first breast, and a display that displays the estimated compression force and compression thickness in a case of imaging a second breast that is the other one of the right breast and the left breast, the device-executable program causing the information processing apparatus to execute:

estimating the compression force and the compression thickness in imaging of the second breast using a learned model that outputs a compression force and a compression thickness of the second breast, which is the other one of the right breast and the left breast, in response to an input of the compression force and the compression thickness of the first breast.

10. A non-transitory device-readable medium for storing a device-executable program for driving an information processing apparatus having a processor that acquires a compression force and a compression thickness, which is a thickness after compression, for a right breast and a compression force and a compression thickness, which is a thickness after compression, for a left breast, the compression force and the compression thickness for the right breast being measured in imaging of the right breast that is a breast on a right side of a subject and the compression force and the compression thickness for the left breast being measured in imaging of the left breast that is a breast on a left side of the subject, and a display that displays whether or not positioning the left breast and the right breast during an instance of imaging is possible, the device-executable program causing the information processing apparatus to execute:

determining whether or not positioning the left breast and the right breast during an instance of imaging is possible using a learned model that outputs a result indicating whether or not the positioning the left breast and the right breast during the instance of imaging is possible in response to an input of the compression force and the compression thickness of the right breast and the compression force and the compression thickness of the left breast.

* * * * *